(12) United States Patent
Zhong et al.

(10) Patent No.: US 10,191,042 B2
(45) Date of Patent: *Jan. 29, 2019

(54) CORE-SHELL NANOPARTICLES WITH MULTIPLE CORES AND METHOD FOR FABRICATING THEM

(71) Applicant: The Research Foundation for The State University of New York, Binghamton, NY (US)

(72) Inventors: Chuan-Jian Zhong, Endwell, NY (US); Hye-Young Park, Seoul (KR)

(73) Assignee: The Research Foundation for the State University of New York, Binghamton, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/960,115

(22) Filed: Apr. 23, 2018

(65) Prior Publication Data

US 2018/0238868 A1    Aug. 23, 2018

Related U.S. Application Data

(60) Continuation of application No. 15/099,129, filed on Apr. 14, 2016, now Pat. No. 10,006,908, which is a
(Continued)

(51) Int. Cl.
| B01J 13/02 | (2006.01) |
| B03C 1/30 | (2006.01) |
| G01N 33/543 | (2006.01) |
| B05D 7/00 | (2006.01) |
| G01N 33/553 | (2006.01) |

(Continued)

(52) U.S. Cl.
CPC ........ *G01N 33/54346* (2013.01); *B01J 13/02* (2013.01); *B03C 1/30* (2013.01); *B05D 7/00* (2013.01); *G01N 33/54326* (2013.01); *G01N 33/54353* (2013.01); *G01N 33/553* (2013.01); *B82Y 15/00* (2013.01); *B82Y 25/00* (2013.01); *B82Y 40/00* (2013.01); *Y10T 428/2991* (2015.01)

(58) Field of Classification Search
CPC ................................................. Y10T 428/2991
USPC ................................................. 428/402–407
See application file for complete search history.

(56) References Cited

U.S. PATENT DOCUMENTS

| 3,239,382 A | 3/1966 | Thompson |
| 3,923,612 A | 12/1975 | Wiesner |

(Continued)

FOREIGN PATENT DOCUMENTS

| EP | 0 557 674 A1 | 9/1993 |
| JP | 6-271905 A | 9/1994 |

OTHER PUBLICATIONS

Buffat et al., "Size Effect on the Melting Temperature of Gold Particles," *Physical Review A* 13(6):2287-98 (1976).
(Continued)

*Primary Examiner* — Alexandre F Ferre
(74) *Attorney, Agent, or Firm* — LeClairRyan PLLC (57) ABSTRACT

The present invention is directed toward core-shell nanoparticles, each comprising a ligand-capped metal shell surrounding a plurality of discrete, nonconcentric, metal-containing cores. Methods of making and using these nanoparticles are also disclosed.

12 Claims, 8 Drawing Sheets

Related U.S. Application Data division of application No. 13/680,749, filed on Nov. 19, 2012, now Pat. No. 9,327,314, which is a division of application No. 12/034,155, filed on Feb. 20, 2008, now Pat. No. 8,343,627.

(60) Provisional application No. 60/890,699, filed on Feb. 20, 2007.

(51) Int. Cl.
 *B82Y 40/00* (2011.01)
 *B82Y 15/00* (2011.01)
 *B82Y 25/00* (2011.01)

(56) References Cited

U.S. PATENT DOCUMENTS

| | | | |
|---|---|---|---|
| 4,554,088 A | 11/1985 | Whitehead et al. | |
| 5,132,193 A | 7/1992 | Reddy et al. | |
| 5,472,577 A | 12/1995 | Portet et al. | |
| 5,560,960 A | 10/1996 | Singh et al. | |
| 5,585,020 A | 12/1996 | Becker et al. | |
| 5,641,723 A | 6/1997 | Bonnemann et al. | |
| 5,789,337 A | 8/1998 | Haruta et al. | |
| 5,876,867 A | 3/1999 | Itoh et al. | |
| 5,985,232 A | 11/1999 | Howard et al. | |
| 6,162,411 A | 12/2000 | Howard et al. | |
| 6,162,532 A | 12/2000 | Black et al. | |
| 6,180,222 B1 | 1/2001 | Schulz et al. | |
| 6,221,673 B1 | 4/2001 | Snow et al. | |
| 6,251,303 B1 | 6/2001 | Bawendi et al. | |
| 6,252,014 B1 | 6/2001 | Knauss | |
| 6,254,662 B1 | 7/2001 | Murray et al. | |
| 6,262,129 B1 | 7/2001 | Murray et al. | |
| 6,322,901 B1 | 11/2001 | Bawendi et al. | |
| 6,344,272 B1 | 2/2002 | Oldenburg et al. | |
| 6,361,944 B1 | 3/2002 | Mirkin et al. | |
| 6,383,500 B1 | 5/2002 | Wooley et al. | |
| 6,458,256 B1 | 10/2002 | Zhong et al. | |
| 6,562,403 B2 | 5/2003 | Klabunde et al. | |
| 6,586,787 B1 | 7/2003 | Shih et al. | |
| 6,645,444 B2 | 11/2003 | Goldstein | |
| 6,730,400 B1 | 5/2004 | Komatsu et al. | |
| 6,773,823 B2 | 8/2004 | O'Connor et al. | |
| 6,818,117 B2 | 11/2004 | Ferguson et al. | |
| 6,818,199 B1 | 11/2004 | Hainfeld et al. | |
| 6,861,387 B2 | 3/2005 | Ruth et al. | |
| 6,872,971 B2 | 3/2005 | Hutchinson et al. | |
| 6,962,685 B2 | 11/2005 | Sun | |
| 6,972,046 B2 | 12/2005 | Sun et al. | |
| 6,984,265 B1 | 1/2006 | Raguse et al. | |
| 7,053,021 B1 | 5/2006 | Zhong et al. | |
| 7,175,912 B2 | 2/2007 | Cui et al. | |
| 7,208,439 B2 | 4/2007 | Zhong et al. | |
| 7,226,660 B2 | 6/2007 | Kuroda et al. | |
| 7,229,690 B2 | 6/2007 | Chan et al. | |
| 7,687,428 B1 | 3/2010 | Thong et al. | |
| 7,811,545 B2 | 10/2010 | Hyeon et al. | |
| 7,829,140 B1 | 11/2010 | Zhong et al. | |
| 7,869,030 B2 | 1/2011 | Zhong et al. | |
| 8,343,627 B2 | 1/2013 | Zhong et al. | |
| 9,327,314 B2 | 5/2016 | Zhong et al. | |
| 2002/0034675 A1 | 3/2002 | Starz et al. | |
| 2002/0160195 A1 | 10/2002 | Halas et al. | |
| 2002/0174743 A1 | 11/2002 | Mukherjee et al. | |
| 2002/0194958 A1 | 12/2002 | Lee et al. | |
| 2003/0004054 A1 | 1/2003 | Ito et al. | |
| 2003/0029274 A1 | 2/2003 | Natan et al. | |
| 2003/0166294 A1 | 9/2003 | Kirby et al. | |
| 2003/0198956 A1 | 10/2003 | Makowski et al. | |
| 2004/0025635 A1 | 2/2004 | Kurihara et al. | |
| 2004/0033345 A1 | 2/2004 | Dubertret et al. | |
| 2004/0055419 A1 | 3/2004 | Kurihara et al. | |
| 2004/0086897 A1 | 5/2004 | Mirkin et al. | |
| 2004/0115345 A1 | 6/2004 | Huang et al. | |
| 2004/0167257 A1 | 8/2004 | Ryang | |
| 2004/0219361 A1 | 11/2004 | Cui et al. | |
| 2004/0245209 A1 | 12/2004 | Jung et al. | |
| 2004/0247924 A1 | 12/2004 | Andres et al. | |
| 2004/0261574 A1 | 12/2004 | Lin et al. | |
| 2005/0025969 A1 | 2/2005 | Berning et al. | |
| 2005/0191231 A1 | 9/2005 | Sun | |
| 2005/0202244 A1 | 9/2005 | Papagianakis | |
| 2005/0235776 A1 | 10/2005 | He et al. | |
| 2005/0265922 A1 | 12/2005 | Nie et al. | |
| 2006/0019098 A1 | 1/2006 | Chan et al. | |
| 2006/0034731 A1 | 2/2006 | Lewis et al. | |
| 2006/0070491 A1* | 4/2006 | Yang | B22F 1/0018 75/255 |
| 2006/0254387 A1 | 11/2006 | Lee et al. | |
| 2006/0286379 A1 | 12/2006 | Gao | |
| 2008/0057001 A1* | 3/2008 | Sun | A61K 49/186 424/9.322 |
| 2016/0231317 A1 | 8/2016 | Zhong et al. | |

OTHER PUBLICATIONS

Carotenuto et al., "Size-Controlled Synthesis of Thiol-Derivatized Gold Clusters," *J. Mater. Chem.* 13(5)1038-41 (2003) (Abstract only).

Han et al., "Core-Shell Nanostructured Nanoparticle Films as Chemically Sensitive Interfaces," *Anal. Chem.* 73:4441-9 (2001).

Han et al., "Nanoparticle-Structured Sensing Array Materials and Pattern Recognition for VOC Detection," *Sensors and Actuators B* 106:431-41 (2005).

Han et al., "Quartz-Crystal Microbalance and Spectrophotometric Assessments of Inter-Core and Inter-Shell Reactivities in Nanoparticle Thin Film Formation and Growth," *J. Mater. Chem.* 11:1258-64 (2001).

Haruta, "Size- and Support-dependency in the Catalysis of Gold," *Catalysis Today* 36:153-166 (1997).

Hostetler et al., "Stable, Monolayer-Protected Metal Alloy Clusters," *J. Am. Chem. Soc.* 120:9396-7 (1998).

Hu et al., "Competitive Photochemical Reactivity in a Self-Assembled Monolayer on a Colloidal Gold Cluster," *J. Am. Chem. Soc.* 123:1464-70 (2001).

Hussain et al., "Preparation of Acrylate-Stabilized Gold and Silver Hydrosols and Gold-Polymer Composite Films," *Langmuir* 19:4831-5 (2003).

Jana et al., "Seeding Growth for Size Control of 5-40 nm Diameter Gold Nanoparticles," *Langmuir* 17:6782-6 (2001).

Kim et al., "Particle Size Control of 11-Mercaptoundecanoic Acid-Protected Au Nanoparticles by Using Heat-Treatment Method," *Chem. Letters* 33(3):344-5 (2004).

Lewis et al., "Melting, Freezing, and Coalescence of Gold Nanoclusters," *Physical Review B* 56(4):2248-57 (1997).

Lou et al., "Gold-platinum Alloy Nanoparticle Assembly as Catalyst for Methanol Electrooxidation," *Chem. Commun.* 473-474 (2001).

Luo et al., "An EQCN Assessment of Electrocatalytic Oxidation of Methanol at Nanostructured Au-Pt Alloy Nanoparticles," *Electrochem. Commun.* 3:172-6 (2001).

Luo et al., "Thermal Activation of Molecularly-Wired Gold Nanoparticles on a Substrate as Catalyst," *J. Am. Chem. Soc.* 124:13988-9 (2002).

Maye et al., "Core-Shell Gold Nanoparticle Assembly as Novel Electrocatalyst of CO Oxidation," *Langmuir* 16(19):7520-7523 (2000).

Maye et al., "Manipulating Core-Shell Reactivities for Processing Nanoparticle Sizes and Shapes," *J. Mater. Chem.* 10:1895-1901 (2000).

Maye et al., "Size-Controlled Assembly of Gold Nanoparticles Induced by a Tridentate Thioether Ligand," *J. Am. Chem. Soc.* 125:9906-7 (2003).

Merriam Webster, New Collegiate Dictionary, G. & C. Merriam Company p. 105 (1979).

Paulus et al., "New PtRu Alloy Colloids as Precursors for Fuel Cell Catalysts," *J. Catalysts* 195:383-393 (2000).

(56) References Cited

OTHER PUBLICATIONS

Sau et al., "Size Controlled Synthesis of Gold Nanoparticles Using Photochemically Prepared Seed Particles," *J. Nanoparticle Res.* 3:257-61 (2001).
Schmid et al., "Ligand-stabilized Metal Clusters and Colloids: Properties and Applications," *J. Chem. Soc.* 5:589-595 (1996).
Shimizu et al., "Size Evolution of Alkanethiol-Protected Gold Nanoparticles by Heat Treatment in the Solid State," *J. Phys. Chem. B* 107:2719-24 (2003).
Sun et al., "Monodisperse FePt Nanoparticles and Ferromagnetic FePt Nanocrystal Superlattices," *Science* 287:1989-92 (2000).
Templeton et al., "Monolayer-Protected Cluster Molecules," *Acc. Chem. Res.* 33:27-36 (2000).
Thomas et al., "Photochemistry of Chromophore-Functionalized Gold Nanoparticles," *Pure Appl. Chem.* 74(9):1731-8 (2002).
Zhai et al., "Regioregular Polythiophene/Gold Nanoparticle Hybrid Materials," *J. Mater. Chem.* 14:141-3 (2004).
Zhong et al., "Core-Shell Assembled Nanoparticles as Catalysts," *Adv. Mater.* 13(19):1507-11 (2001).
Zhong et al., "Electrode Nanomaterials Self-Assembled from Thiolate-Encapsulated Gold Nanocrystals," *Electrochem. Commun.* 1:72-77 (1999).
Brust et al., "Synthesis of Thiol-derivatised Gold Nanoparticles in a Two-phase Liquid-Liquid System," *J. Chem. Soc. Chem. Commun.* 801-2 (1994).
Chen & Sommers, "Alkanethiolate-Protected Copper Nanoparticles: Spectroscopy, Electrochemistry, and Solid-State Morphological Evolution," *J. Phys. Chem.* 105(37):8816-20 (2001).
Clarke et al., "Size-Dependent Solubility of Thiol-Derivatized Gold Nanoparticles in Supercritical Ethane," *Langmuir* 17(20):6048-50 (2001).
Daniel & Astruc, "Gold Nanoparticles: Assembly, Supramolecular Chemistry, Quantum-Size-Related Properties, and Applications Toward Biology, Catalysis, and Nanotechnology," *Chem. Rev.* 104(1):293-346 (2004).
Fan et al., "Ordered Nanocrystal/Silica Particles Self-assembled from Nanocrystal Micelles and Silicate," *Chem. Commun.* 2323-5 (2006).
Ito et al., "Medical Application of Functionalized Magnetic Nanoparticles," *J. Biosci. Bioeng.* 100(1):1-11 (2005).
Leibowitz et al., "Structures and Properties of Nanoparticle Thin Films Formed via a One-Step Exchange—Cross-Linking—Precipitation Route," *Anal. Chem.* 71(22):5076-83 (1999).
Lu et al., "Magnetic Nanoparticles: Synthesis, Protection, Functionalization, and Application," *Angew. Chem. Int. Ed.* 46:1222-44 (2007).
Luo et al., "AFM Probing of Thermal Activation of Molecularly Linked Nanoparticle Assembly," *J. Phys. Chem.* 108(28):9669-77 (2004).
Maye et al., "Heating-Induced Evolution of Thiolate-Encapsulated Gold Nanoparticles: A Strategy for Size and Shape Manipulations," *Langmuir* 16(2):490-7 (2000).
Park et al., "Fabrication of Magnetic Core@Shell Fe Oxide@Au Nanoparticles for Interfacial Bioactivity and Bio-separation," *Langmuir* 23(17):9050-6 (2007).
Schadt et al., "Molecularly Tuned Size Selectivity in Thermal Processing of Gold Nanoparticles," *Chem. Mater.* 18(22):5147-9 (2006).
Shaffer et al., "Comparison Study of the Solution Phase Versus Solid Phase Place Exchange Reactions in the Controlled Functionalization of Gold Nanoparticles," *Langmuir* 20(19):8343-51 (2004).
Teranishi et al., "Heat-Induced Evolution of Gold Nanoparticles in the Solid State," *Adv. Mater.* 13:1699-701 (2001).
Terzi et al., "3-Methylthiophene Self-Assembled Monolayers on Planar and Nanoparticle Au Surfaces," *J. Phys. Chem.* 109(41):19397-402 (2005).
Wang et al., "Monodispersed Core—Shell Fe3O4@Au Nanoparticles," *J. Phys. Chem.* 109(46):21593-601 (2005).
Xia et al., "Monodispersed Colloidal Spheres: Old Materials with New Applications," *Adv. Mater.* 12:693-713 (2000).
Zhong et al., "Size and Shape Evolution of Core-shell Nanocrystals," *Chem. Commun.* 1211-12 (1999).
Barazzouk et al., "Photoinduced Electron Transfer Between Chlorophyll $\alpha$ and Gold Nanoparticles," *J. Phys. Chem.* 109(2):716-23 (2005).
Chandrasekharan et al., "Dye-Capped Gold Nanoclusters: Photoinduced Morphological Changes in Gold/Rhodamine 6G Nanoassemblies," *J. Phys. Chem.* 104(47):11103-9(2000).
Dulkeith et al., "Gold Nanoparticles Quench Fluorescence by Phase Induced Radiative Rate Suppression," *Nano Lett.* 5(4):585-9 (2005).
Ghosh et al., "Fluorescence Quenching of 1-methylaminopyrene Near Gold Nanoparticles: Size Regime Dependence of the Small Metallic Particles," *Chemical Physics Letters* 395:366-72 (2004).
Grabar et al., "Preparation and Characterization of Au Colloid Monolayers," *Anal. Chem.* 67(4):735-43 (1995).
Han et al., "Novel Interparticle Spatial Properties of Hydrogen-Bonding Mediated Nanoparticle Assembly," *Chem. Mater.* 15(1):29-37 (2003).
Hannah & Armitage, "DNA-Templated Assembly of Helical Cyanine Dye Aggregates: A Supramolecular Chain Polymerization," *Acc. Chem. Res.* 37(11):845-53 (2004).
Huang & Murray, "Quenching of $[Ru(bpy)_3]^{2+}$ Fluorescence by Binding to Au Nanoparticles," *Langmuir* 18(18):7077-81 (2002).
Israel et al., "Electroactivity of $Cu^{2+}$ at a Thin Film Assembly of Gold Nanoparticles Linked by 11-mercaptoundecanoic Acid," *Journal of Electroanalytical Chemistry* 517:69-76 (2001).
Kneipp et al., "Optical Probes for Biological Applications Based on Surface-Enhanced Raman Scattering from Indocyanine Green on Gold Nanoparticles," *Anal. Chem.* 77(8):2381-5 (2005).
Kometani et al., "Preparation and Optical Absorption Spectra of Dye-Coated Au, Ag, and Au/Ag Colloidal Nanoparticles in Aqueous Solutions and in Alternate Assemblies," *Langmuir* 17(3):578-80 (2001).
Lian et al., "Ultrasensitive Detection of Biomolecules with Fluorescent Dye-doped Nanoparticles," *Analytical Biochemistry* 334:135-44 (2004).
Lim et al., "Absorption of Cyanine Dyes on Gold Nanoparticles and Formation of J-Aggregates in the Nanoparticle Assembly," *J. Phys. Chem.* 110(13):6673-82 (2006).
Lim et al., "Kinetic and Thermodynamic Assessments of the Mediator—Template Assembly of Nanoparticles," *J. Phys. Chem.* 109(7):2578-83 (2005).
Lim et al., "Multifunctional Fullerene-Mediated Assembly of Gold Nanoparticles," *Chem. Mater.* 17(26):6528-31 (2005).
Lu et al., "Surface-Enhanced Superquenching of Cyanine Dyes as J-Aggregates on Laponite Clay Nanoparticles," *Langmuir* 18(20):7706-13 (2002).
Maye et al., "Gold and Alloy Nanoparticles in Solution and Thin Film Assembly: Spectrophotometric Determination of Molar Absorptivity," *Analytica Chimica Acta* 496:17-27 (2003).
Templeton et al., "Redox and Fluorophore Functionalization of Water-Soluble, Tiopronin-Protected Gold Clusters," *J. Am. Chem. Soc.* 121(30):7081-9 (1999).
Thomas & Kamat, "Chromophore-Functionalized Gold Nanoparticles," *Acc. Chem. Res.* 36(12):888-98 (2003).
Wang et al., "DNA Binding of an Ethidium Intercalator Attached to a Monolayer-Protected Gold Cluster," *Anal. Chem.* 74(17):4320-7 (2002).
Wiederrecht et al., "Coherent Coupling of Molecular Excitons to Electronic Polarizations of Noble Metal Nanoparticles," *Nano Lett.* 4(11):2121-5 (2004).
Zamborini et al., "Electron Hopping Conductivity and Vapor Sensing Properties of Flexible Network Polymer Films of Metal Nanoparticles," *J. Am. Chem. Soc.* 124(30):8958-64 (2002).
Zhang et al., "Colorimetric Detection of Thiol-containing Amino Acids Using Gold Nanoparticles," *Analyst* 127:462-5 (2002).
Zheng et al., "Imparting Biomimetic Ion-Gating Recognition Properties to Electrodes with a Hydrogen-Bonding Structures Core—Shell Nanoparticle Network," *Anal. Chem.* 72(10):2190-9 (2000).
Luo et al., "Synthesis and Characterization of Monolayer-Capped PtVFe Nanoparticles With Controllable Sizes and Composition," *Chem. Mater.* 17:5282-5290 (2005).

(56) References Cited

OTHER PUBLICATIONS

Luo et al., "Ternary Alloy Nanoparticles with Controllable Sizes and Composition and Elecrocatalytic Activity," *J. Mater. Chem.* 16:1665-1673 (2006).
Kariuki et al., "Assembly of Bimetallic Gold-Silver Nanoparticles via Selective Interparticle Dicarboxylate-Silver Linkages," *Chem. Mater.* 18:123-132 (2006).
Huie, "Guided Molecular Self-Assembly: A Review of Recent Efforts," *Smart Mater. Struct.* 12:264-271 (2003).
Yang et al., "Effect of Ultrasonic Treatment on Dispersibility of Fe3O4 Nanoparticles and Synthesis of Multi-Core Fe3O4/SiO2 Core/Shell Nanoparticles," *J. Mater. Chem.* 15:4252-4257 (2005).
Cushing et al., "Synthesis and Magnetic Properties of Au-Coated Amorphouse Fe20ni80 Nanoparticles," *Journal of Physics and Chemistry of Solids* 65:825-829 (2004).
Casavola, et. al., "Colloidal Strategies for Preparing Oxide-Based Hybrid Nanocrystals," *Eur. J. Inorg. Chem.* pp. 837-54 (2008).
Park et al.., "Fabrication of Magnetic Core@Shell Fe Oxide@Au Nanoparticles for Interfacial Bioactivity and Bio-separation," *Langmuir* 23:9050-56 (2007).
Lyon et al., Nano Letters 4(4):719-723 (2004).
Wang et al., J. Mater. Chem. 15:1821-1832 (2005).

\* cited by examiner

CORE-SHELL NANOPARTICLES WITH
MULTIPLE CORES AND METHOD FOR
FABRICATING THEM

This application is a continuation of U.S. patent application Ser. No. 15/099,129, filed Apr. 14, 2016, which is a division of U.S. patent application Ser. No. 13/680,749, filed Nov. 19, 2012, now U.S. Pat. No. 9,327,314, issued May 3, 2016, which is a division of U.S. patent application Ser. No. 12/034,155, filed Feb. 20, 2008, now U.S. Pat. No. 8,343,627, issued Jan. 1, 2013, which claims the benefit of U.S. Provisional Patent Application Ser. No. 60/890,699, filed Feb. 20, 2007, which are hereby incorporated by reference in their entirety.

This invention was made with government support under grant number CHE0349040 awarded by the National Science Foundation. The government has certain rights in this invention.

FIELD OF THE INVENTION

The present invention relates to core-shell nanoparticles with multiple cores and a method for fabricating them.

BACKGROUND OF THE INVENTION

Nanoparticles exhibit intriguing changes in electronic, optical, and magnetic properties as a result of the nanoscale dimensionality (Daniel et al., Chem. Rev. 104:293 (2004); Xia et al., *Adv. Mater.* 12:693 (2000)). The ability to engineer size and monodispersity is essential for the exploration of these properties. The preparation of magnetic nanoparticles and nanocomposites has attracted both fundamental and practical interest because of potential applications in areas such as ferrofluids, medical imaging, drug targeting and delivery, cancer therapy, separations, and catalysis (Kim et al., *J. Magn. Magn. Mater.* 225:256 (2001); Niemeyer, *Angew. Chem. Int. Ed.* 40:4128 (2001); Neuberger et al., *J. Magn. Magn. Mater.* 293:483 (2005); Tartaj et al., *J. Magn. Magn. Mater.* 290:28 (2005); Dobson, *Drug Dev. Res.* 67:55 (2006)). However, one of the major obstacles is the lack of flexibility in surface modification and biocompatibility. Gold coating on magnetic particles provides an effective way to overcome such an obstacle via well-established surface chemistry to impart magnetic particles with the desired chemical or bio-medical properties (Daniel et al., *Chem. Rev.* 104:293 (2004); Xia et al., *Adv. Mater.* 12:693 (2000)). There have been reports on the synthesis of gold-coated magnetic core-shell particles by various methods, e.g. gamma ray, laser ablation, sonochemical method, layer-by-layer electrostatic deposition, chemical reduction, and micelle methods (Kinoshita et al., *J. Magn. Magn. Mater.* 293:106 (2005); Zhang et al., *J. Phys. Chem. B* 110:7122 (2006); Caruntu et al., *Chem. Mater.* 17:3398 (2005); Spasova et al., *J. Mater. Chem.* 15:2095 (2005); Stoeva et al., *J. Am. Chem. Soc* 127:15362 (2005); Lyon et al., *Nano Letters* 4:719 (2004); Mandal et al., *J. Colloid Interface Sci.* 286:187 (2005)). Recently reported was the synthesis of monodispersed core-shell Fe oxide-Au nanoparticles via coating pre-synthesized iron oxide nanoparticles (5-7 nm sizes) with gold shells (1-2 nm) (Wang et al., *J. Phys. Chem. B* 109:21593 (2005)). However, many of the magnetic core or shell dimensions have been limited to <15 nm. This limitation poses a serious barrier to magnetic applications where the size tunability, especially in larger sizes (up to ~100 nm) with sufficient magnetization, is required.

The present invention is directed to overcoming these deficiencies in the art.

SUMMARY OF THE INVENTION

One aspect of the present invention is directed toward core-shell nanoparticles, each comprising a ligand-capped metal shell surrounding a plurality of discrete, nonconcentric, metal-containing cores.

Another aspect is directed to a method of producing core-shell nanoparticles, each comprising a ligand-capped metal shell surrounding one or more metal-containing cores. This method includes providing ligand-capped metal-containing core material nanoparticles and ligand-capped metal shell material nanoparticles. These nanoparticles are reacted under conditions effective to produce the core-shell nanoparticles comprising a ligand-capped metal shell surrounding one or more metal-containing cores.

A further aspect of the present invention is directed to a method of separating a target molecule from a sample. In accordance with this method, core-shell nanoparticles, each comprising a ligand-capped metal shell surrounding a plurality of discrete, nonconcentric, metal-containing cores are provided, with a first binding material bound to the ligand-capped shell. The binding material that specifically binds to the target molecule is incubated with the sample in a reaction vessel under conditions effective for the first binding material to bind to the target molecule. The reaction vessel is contacted with a magnet under conditions effective to immobilize the nanoparticles in the reaction vessel. The immobilized nanoparticles may be recovered.

Disclosed herein is a novel thermal approach to the fabrication of core-shell magnetic nanoparticles with not only high monodispersity but also size tunability in the 5-100 nm range. The basic idea explores the viability of hetero-interparticle coalescence between gold and magnetic nanoparticles under encapsulating environment for creating core-shell type nanoparticles in which the magnetic core consists of single or multiple metal cores with a pomegranate-like interior structure depending on the degree of coalescence (see FIG. 1).

This approach is new and differs from previous methods for synthesizing gold-coated Fe-Oxide particles in two significant ways: First, the present method uses a thermal evolution method starting from Fe-Oxide nanoparticles and Au nanoparticles as precursors, whereas the previous synthesis method uses Fe-Oxide nanoparticles and Au(Ac)$_3$ molecules as precursors. Second, the present method produces golden magnetic particles with either single core or multiple cores, whereas the previous method produces golden magnetic particles with only a single core.

This approach is also new in comparison with the homo-interparticle coalescence demonstrated for evolving the sizes of gold nanoparticles by a thermally-activated evolution (Zhong et al, *Chem. Comm.* 13:1211 (1999); Maye et al., *Langmuir* 16:490 (2000), which are hereby incorporated by reference in their entirety). In the previous method interparticle coalescence of metals or alloys is utilized for evolving the sizes of gold or alloy nanoparticles. In the present method, it is hetero-coalescence between Fe-oxide nanoparticles and gold nanoparticles for evolving single core Fe-Oxide-Au nanoparticles and multiple-core (Fe-Oxide)$_n$-Au nanoparticles. The competition between growing Au, Fe-oxide-Au, and the pomegranate-like core-shell nanoparticles is determined by solution temperature, composition and capping structures. This approach could serve as a simple and effective strategy for monodispersed Fe-oxide-Au nanoparticles of controlled sizes.

BRIEF DESCRIPTION OF THE DRAWINGS

FIG. 1 is a schematic drawing illustrating the hetero-interparticle coalescence of nanoparticles. Component 1A represents ligand-capped metal shell material nanoparticles. Component 1B represents ligand-capped metal-containing core material nanoparticles. Component A and B combine to form nanoparticles (i.e. Component C) comprising a ligand-capped metal shell surrounding a single metal-containing core. Component C coalesces to form component D which is a nanoparticle comprising a ligand-capped metal shell surrounding a plurality of discrete, nonconcentric, metal-containing cores.

FIGS. 3A-B are TEM micrographs of gold nanoparticles produced by thermal processing (149° C.) of $Au_{2nm}$-DT nanoparticles. FIG. 3A shows the precursor nanoparticles 2.0±0.4 nm and FIG. 3B shows the product nanoparticles (6.4±0.4 nm).

FIGS. 4A-B are TEM images of OA/OAM-capped $Fe_2O_3$ nanoparticles produced by thermal processing (149° C.): before (FIG. 4A, 4.4±0.3 nm) and after (FIG. 4B, 4.5±0.5 nm) thermal processing.

FIGS. 5A-C are TEM images for precursor $Fe_2O_3$ (FIG. 5A), Au (FIG. 5B), and thermally-evolved Au-coated $Fe_2O_3$ nanoparticles using 25:1 ratio of Au to $Fe_2O_3$ nanoparticles (FIG. 5C).

FIGS. 6A-B are TEM images of the nanoparticles thermally evolved from the same nanoparticles precursors but with two different molar ratios of Au nanoparticles to $Fe_2O_3$ nanoparticles, (FIG. 6A) $Au:Fe_2O_3$=25:1, and (FIG. 6B) $Au:Fe_2O_3$=132:1.

FIGS. 7A-D are TEM images of nanoparticles obtained from the same precursor molar ratios ($Au:Fe_2O_3$=5:1) but using different capping agents on $Fe_2O_3$: OA-capped $Fe_2O_3$ (FIG. 7A), OA-capped $Fe_2O_3$ (FIG. 7B), OAM-capped $Fe_2O_3$ (FIG. 7C), and OA/OAM-capped $Fe_2O_3$ in a ~2× reaction volume (FIG. 7D).

FIGS. 9A-B are SERS spectra for MBA label which are incorporated onto OA-OAM capped $Fe_2O_3$@Au nanoparticles (FIG. 9A) and protein-A capped Au nanoparticles (FIG. 9B).

FIGS. 10A-C is a photograph showing magnetic properties of $Fe_2O_3$@Au nanoparticles dissolved in toluene (FIG. 10A), suspended in ethanol-toluene (FIG. 10B), and after applying a magnet to the suspension of FIG. 10B (FIG. 10C).

FIGS. 11A-B are FTIR spectra of OA/OM-capped core@shell $Fe_2O_3$@Au particles before (FIG. 11A) and after (FIG. 11B) ligand exchange reaction with MUA.

DETAILED DESCRIPTION OF THE INVENTION

One aspect of the present invention is directed toward core-shell nanoparticles, each comprising a ligand-capped metal shell surrounding a plurality of discrete, nonconcentric, metal-containing cores. The core-shell nanoparticles may be present in a monodispersion with controlled diameters ranging from 5 nm to 100 nm.

The metal-containing cores may be magnetic, paramagnetic or superparamagnetic. The metal of the metal-containing cores may be iron (e.g., $Fe_3O_4$ or $Fe_2O_3$), magnesium, cobalt, or mixtures thereof.

The metal of the metal shell may be gold, silver, platinum, rhodium, palladium, vanadium, titanium, iron, cobalt, magnesium, ruthenium, chromium, molybdenum, tantalum, zirconium, manganese, tin, or mixtures thereof.

The capping ligand may be decanethiolate, oleylamine, oleic acid, acrylates, N,N-trimethyl(undecylmercapto)ammonium (TUA), tetrabutylammonium tetrafluoroborate (TBA), tetramethylammonium bromide (TMA), cetyltrimethylammonium bromide (CTAB), citrates, poly methacrylate, ascorbic acid, DNA, 2-mercaptopropionic acid (MPA), 3-mercaptopropionic acid (MPA), 11-mercaptoundecanoic acid (MUA), 10-mercaptodecane-1-sulfonic acid, 16-mercaptohexadecanoic acid, diimide, N-(2-mercaptopropionyl)glycine (tiopronin), 2-mercaptoethanol, 4-mercapto-1-butanol, dodecyl sulfate, amino acids, homocysteine, homocystine, cysteine, cystine, glutathione, mercaptobenzoic acid (MBA), Protein A, bovine serum albumin (BSA), or anti-rabbit-IgG (Ab).

The core-shell nanoparticles may further comprise a binding material bound to the ligand-capped shell. The binding material may be proteins, peptides, antibodies, or antigens.

Another aspect is directed to a method of producing core-shell nanoparticles, each comprising a ligand-capped metal shell surrounding one or more metal-containing cores. This method includes providing ligand-capped metal-containing core material nanoparticles and ligand-capped metal shell material nanoparticles. These nanoparticles are reacted under conditions effective to produce the core-shell nanoparticles comprising a ligand-capped metal shell surrounding one or more metal-containing cores.

Figure 1:
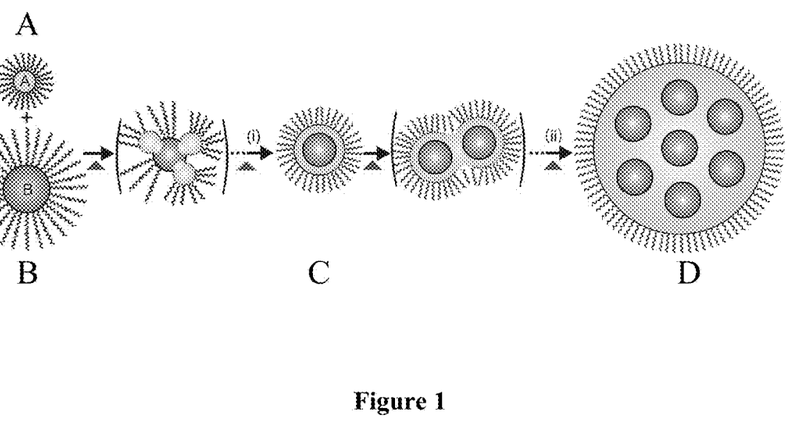

As shown in FIG. 1, the method of the present invention provides for hetero-interparticle coalescence of ligand-capped metal shell material nanoparticles, e.g., decanethiolate (DT)-capped Au (Component A) and ligand-capped metal-containing core material nanoparticles, e.g., oleic acid or oleylamine (OA/OM)-capped $Fe_2O_3$ (Component B). Thermal evolution results in the formation of nanoparticles comprising a ligand-capped metal shell surrounding a single metal-containing core (Component C). These single-core nanoparticles can undergo further thermal evolution to form nanoparticles comprising a ligand-capped metal shell surrounding a plurality of discrete, nonconcentric, metal-containing cores (Component D).

The specific materials used to form these ligand-capped metal shell surrounding one or more metal containing cores and the structure of the nanoparticles themselves are substantially the same as those described above.

The reaction conditions may include combining the ligand-capped metal-containing core material nanoparticles and the ligand-capped metal shell material nanoparticles in a solvent to form a reaction mixture. The reaction mixture is heated under conditions effective to form the core-shell nanoparticles comprising a ligand-capped metal shell surrounding one or more metal-containing cores.

The solvent may include toluene, tetraoctylammonium bromide, and/or decanethiols and may be heated to a temperature of 140-160° C.

The core-shell nanoparticles may be subjected to one or more sizing operations, such as centrifugation.

A further aspect of the present invention is directed to a method of separating a target molecule from a sample. In accordance with this method, core-shell nanoparticles, each comprising a ligand-capped metal shell surrounding a plurality of discrete, nonconcentric, metal-containing cores are provided, with a first binding material bound to the ligand-capped shell. The binding material that specifically binds to the target molecule is incubated with the sample in a reaction vessel under conditions effective for the first binding material to bind to the target molecule. The reaction vessel is contacted with a magnet under conditions effective to immobilize the nanoparticles in the reaction vessel. The immobilized nanoparticles may be recovered.

The method may include removing liquids from the reaction vessel. Once the nanoparticles with binding materials are bound to the target in a sample solution and the vessel is contacted with a magnet thereby immobilizing the nanoparticles-target complex, all or some of the sample solution can be removed for further purification, analysis, or other use. The liquids can be removed by various means well known in the art including pumping, pouring, pipetting, or evaporation.

Furthermore, the target molecules may be separated from the nanoparticles. Target molecules may be reversibly bound to the binding material or the binding material may be reversibly bound to the nanoparticles, allowing separation of the target molecules from the nanoparticles by various methods known in the art such as solvation, exchange, heating, or digestion.

The binding material may be proteins, peptides, antibodies, antigens or other suitable material known in the art.

Magnetic separation techniques are commonly used for the purification, quantification, or identification of various substances (see Ito et al., *J. Biosci. Bioeng.* 100(1):1-11 (2005); Alexiou et al., *J. Nanosci. Nanotechnol.,* 6:2762 (2006); and Risoen et al., *Protein Expr. Purif.* 6(3):272-7 (1995), which are hereby incorporated by reference in their entirety). The term "magnetic particles" is meant to include particles that are magnetic, paramagnetic, or superparamagnetic properties. Thus, the magnetic particles are magnetically displaceable but are not necessarily permanently magnetizable. Methods for the determination of analytes using magnetic particles are described, for example, in U.S. Pat. No. 4,554,088, which is hereby incorporated by reference in its entirety.

The magnetic particle may be bound to an affinity ligand, the nature of which will be selected based on its affinity for a particular analyte whose presence or absence in a sample is to be ascertained. The affinity molecule may, therefore, comprise any molecule capable of being linked to a magnetic particle which is also capable of specific recognition of a particular analyte. Affinity ligands, therefore, include monoclonal antibodies, polyclonal antibodies, antibody fragments, nucleic acids, oligonucleotides, proteins, oligopeptides, polysaccharides, sugars, peptides, peptide encoding nucleic acid molecules, antigens, drugs, and other ligands.

The target material may optionally be a material of biological or synthetic origin. For examples, such target materials may be antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatised nucleic acids, DNA, RNA, natural or synthetic drugs, receptors, virus particles, bacterial particles, virus components, cells, cellular components, and natural or synthetic lipid vesicles.

Figure 2A:
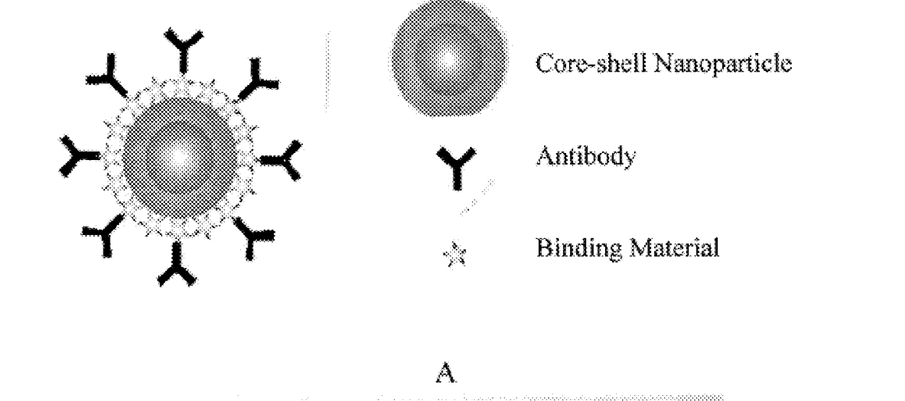
FIG. 2A shows a schematic drawing of a core-shell nanoparticle with binding material and antibodies bound to the core-shell nanoparticle.
Figure 2B:
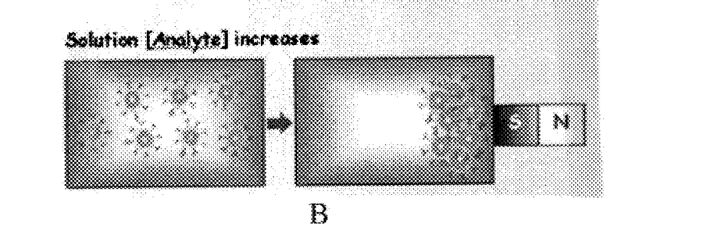
FIG. 2B-C are schematic drawings of methods of concentrating target analytes using magnetic nanoparticles.
Figure 2C:
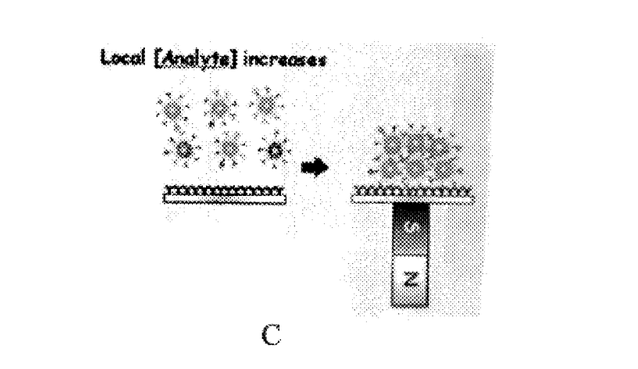

Magnetic particles have potential to be used in imaging and analytical detection assays as well. For example, in a Surfaced Enhanced Raman Spectroscopy (SERS)-based assay, increasing analyte concentration in solution or local analyte concentration at an assay surface can significantly improve the limits of detection of different analytes, especially of large biomolecules such as bacteria and viruses. FIG. 2A shows a representation of antibodies, for example, bound to a magnetic core-shell nanoparticle. Such a system could be used to bind a target forming a nanoparticle-target complex. Application of a magnetic field will allow immobilization of the nanoparticle-target complex (FIG. 2B). Alternatively, through the application of a magnetic field, the nanoparticle-target complex can be concentrated at the site of an assay surface (FIG. 2C) allowing for detection or improvement of the limits of detection.

During recent years, there has been in increase in interest regarding the use of magnetic nanoparticles as contrast agents for use in conjunction with magnetic resonance imaging (MRI) techniques (Ito et al., *J. Biosci. Bioeng.* 100:1-11 (2005), which is hereby incorporated by reference in its entirety). Magnetic nanoparticles have also been proposed for use in direct sensing methods for diagnosis of cancer (Suzuki et al., *Brain Tumor Pathol.* 13:127 (1996), which is hereby incorporated by reference in its entirety) and for novel tissue engineering methodologies utilizing magnetic force and functionalized magnetic nanoparticles to manipulate cells (Ito et al., *J. Biosci. Bioeng.* 100:1-11 (2005), which is hereby incorporated by reference in its entirety).

In therapeutic applications, for example, application of a magnetic field to the patient may serve to target drug-carrying magnetic particles to a desired body site. In many cases, the dose of systemically administered chemotherapeutics is limited by the toxicity and negative side effects of the drug. Therapeutically sufficient concentrations of the drugs in the respective tissues often need to be quite high. Magnetic carrier systems should allow targeted drug delivery to achieve such high local concentrations in the targeted tissues, thereby minimizing the general distribution throughout the body. Special magnetic guidance systems can direct, accumulate, and hold the particles in the targeted area, for example, a tumor region (Alexiou et al., *J. Nanosci. Nanotechnol.* 6:2762 (2006), which is hereby incorporated by reference in its entirety).

EXAMPLES

The following examples are intended to illustrate the invention, and are not intended to limit its scope.

Example 1—Chemicals

Iron pentacarbonyl ($Fe(CO)_5$), phenyl ether, trimethylamine oxide, decanethiol (DT) tetraoctylammonium bromide (TOA-Br), oleylamine (OAM), oleic acid (OA), trimethylamine oxide dihydreate (($CH_3)_3NO.2H_2O$), bovine serum albumin (BSA), 11-mercaptoundecanoic acid (MUA), mercaptobenzoic acid (MBA), dithiobis (succinimidyl propionate) (DSP), and other solvents (hexane, toluene, and ethanol) were obtained form Aldrich and were used as received. Anti-rabbit IgG and rabbit IgG were purchased from Pierce. Protein A and gold nanoparticles were obtained from Ted Pella.

Example 2—Synthesis and Preparation $Fe_2O_3$ ($\gamma$-$Fe_2O_3$) nanoparticles and Au nanoparticles were synthesized by known protocols, whereas the preparation of $Fe_2O_3$@Au nanoparticles was based on a new protocol developed in this work. For the synthesis of $Fe_2O_3$ nanoparticles, $Fe_2O_3$ nanoparticles capped with OA (and/or OAM) were prepared based on the modified procedure reported previously (Wang et al., *J Phys. Chem. B* 109:21593 (2005), which is hereby incorporated by reference in its entirety). Briefly, 0.74 mL of $Fe(CO)_5$ and 5.3 mL of OA (and/or OAM) in 40 mL of phenyl ether was stirred at 100° C. under argon purge. The solution was heated to 253° C. and refluxed for 1 h. The solution turned to dark brown. After the solution was cooled to room temperature, 1.26 g of ($CH_3)_3NO.2H_2O$ was added and stirred at 130° C. for 2 h. Temperature was increased to 253° C. and refluxed for 2 h. The reaction solution was stirred overnight. The resulting nanoparticles were precipitated with ethanol and rinsed multiple times. Finally, particles were dispersed in hexane or toluene. For the synthesis of Au nanoparticles, the standard two-phase method reported by Brust and Schriffrin (*J. Chem. Soc., Chem. Commun.* 1994:801-802, which is hereby incorporated by reference in its entirety) was used. Gold nanoparticles of 2 nm diameter encapsulated with DT monolayer shells ($Au_{2nm}$-DT) were synthesized.

For the preparation of $Fe_2O_3$@Au nanoparticles, a modified strategy of thermally-activated processing protocol (Schadt et al., *Chem. Mater.* 18:5147 (2006); Maye et al., *Langmuir* 16:490 (2000); Zhong et al., *Chem. Commun.* 13:1211 (1999), which are hereby incorporated by reference in their entirety) was used. The thermal processing treatment of Au nanoparticles involved molecular desorption, nanoscrystal core coalescence, and molecular re-encapsulation processes in the evolution of nanoparticle precursors at elevated temperatures (149° C.). The thermal processing of small-sized monolayer-protected nanoparticles as precursors (Schadt et al., *Chem. Mater.* 18:5147 (2006); Maye et al., *Langmuir* 16:490 (2000); Zhong et al., *Chem. Commun.* 13:1211 (1999), which are hereby incorporated by reference in their entirety) has recently gained increasing interest for processing nanoparticle size and monodispersity (Clarke et al., *Langmuir* 17:6048-6050 (2001); Teranishi et al., *Adv. Mater.* 13:1699-1701 (2001); Fan et al., *Chem. Commun.* 2006:2323-2325; Terzi et al., *J. Phys. Chem. B* 109:19397-19402 (2005); Shaffer et al., *Langmuir* 20:8343-8351 (2004); Chen et al., *J. Phys. Chem. B* 105:8816-8820 (2001), which are hereby incorporated by reference in their entirety). In a typical thermal processing treatment, 1.4 mL of $Au_{2nm}$-DT and $Fe_2O_3$ nanoparticles in toluene with various ratio was placed in a reaction tube. The mixed precursor solution contained $Au_{2nm}$-DT, OA- and/or OAM-$Fe_2O_3$ nanoparticles, toluene, and TOA-Br. The tube was then placed in a preheated Yamato DX400 Gravity Convection Oven at 149° C. for 1-hour. Temperature variation from this set point was limited to ±1.5° C. After the 1-hour thermal treatment, the reaction tube was allowed to cool down and the particles were redispersed in toluene. The above approach can also be used to produce $Fe_3O_4$@Au nanoparticles. The term "Fe-oxide" was used to refer to a variety of iron oxides, including $Fe_2O_3$ and $Fe_3O_4$.

Example 3—Preparation of Nanoparticles Capped with Proteins and SERS Labels

The as-synthesized DT-capped iron oxide@Au particles were transferred to water by ligand exchange using mercaptoundecanoic acid (MUA) by following a procedure reported by Gittins et al. (*Chem. Phys. Chem.* 3(1):110-113 (2002), which is hereby incorporated by reference in its entirety), with a slight modification. The nanoparticles were further modified with DSP for protein coupling by ligand exchange. To 1 mL solution of DT-capped iron oxide@Au particles (6 ng/mL) in borate buffer (pH 8.3), 140 µL of 1 mM DSP was added and stirred overnight. The nanoparticles were rinsed with centrifuge and 204, of anti-Rabbit IgG (2.4 mg/mL) was pipetted. After overnight incubation, the particles were centrifuged three times and finally resuspended in 2 mM Tris buffer (pH 7.2) with 1% BSA and 0.1% Tween 80. The same method was also used for coating protein A and BSA to Au nanoparticles of 80 nm size. 2.5 µL of 1 mM DSP was added to 1 mL of Au particles (80 nm, $1\times10^{10}$/mL) and reacted overnight. 40 µL of 50 mM borate buffer was added and either protein A or BSA was added to make final concentration of protein A or BSA to be ~25 µg/mL. MBA was used as a Raman label (Ni et al., *Anal. Chem.*, 71:4903 (1999), which is hereby incorporated by reference in its entirety). To introduce spectroscopic label onto the Au nanoparticles modified with either protein A or BSA, an ethanolic solution of MBA (10 µg/mL) was added and reacted overnight. Finally, the particles were centrifuged three times and finally re-suspended in 2 mM Tris buffer (pH 7.2) with 1% BSA and 0.1% Tween 80. The resulting protein capped nanoparticles were stored at 4° C.

Example 4—Measurements and Instrumentation

The study of the binding between Au nanoparticles labeled with protein A (or BSA) and MBA (A) and iron oxide@Au nanoparticles labeled with anti-rabbit IgG (B) was carried out by mixing (A) and (B). 250 µL of (A) was first diluted in 1750 µL tris buffer before mixing with ~10 µL of (B). UV-vis spectra were collected immediately following gentle mixing of the solution. Spectroscopic measurements were performed after using magnet to collect the reaction product. For spectroscopic labeling, 0.8 mL of ethanolic solution of MBA was added to 0.5 mL of iron oxide@Au particles (30 mg/mL in toluene), and shaked overnight. The particles were cleaned three times with toluene and ethanol and dispersed in 2 mM borate buffer. The particles were then drop cast on gold on mica surface.

Example 5—Surface-Enhanced Raman Scattering (SERS)

Raman spectra were recorded using the Advantage 200A Raman instrument (DeltaNu). The instrument collects data over 200 to 3400 cm$^{-1}$. The laser power was 5 mW and the wavelength of the laser was 632.8 nm. In the experiment, the spectrum in the range from 200 to 1500 cm$^{-1}$ was collected.

Example 6—Transmission Electron Microscopy (TEM)

TEM micrographs of the particles were obtained using a Hitachi H-7000 Electron Microscope operated at 100 kV. The particles dispersed in hexane were drop cast onto a carbon film coated copper grid followed by evaporation at room temperature.

Example 7—Ultraviolet-Visible Spectroscopy (UV-Vis)

UV-Vis spectra were acquired with a HP8453 spectrophotometer. The spectra were collected over the range of 200-1100 nm.

Example 8—Direct Current Plasma-Atomic Emission Spectroscopy (DCP-AES)

The composition of synthesized particles and thin films was analyzed using DCP-AES. Measurements were made on emission peaks at 267.59 nm and 259.94 nm, for Au and Fe, respectively. The nanoparticle samples were dissolved in concentrated aqua regia, and then diluted to concentrations in the range of 1 to 50 ppm for analysis. Calibration curves were constructed from standards with concentrations from 0 to 50 ppm in the same acid matrix as the unknowns. Detection limits, based on three standard deviations of the background intensity are 0.008 ppm and 0.005 ppm for Au and Fe, respectively. Standards and unknowns were analyzed 10 times each for 3 second counts. Instrument reproducibility, for concentrations greater than 100 times the detection limit, results in <2% error.

Figure 3A:
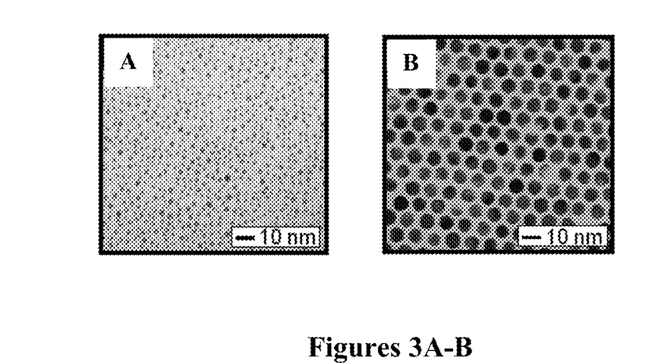

Example 9—Morphological Characterization of the Core-Shell Magnetic Nanoparticles Since the thermal processing treatment involved molecular desorption, nanocrystal core coalescence, and molecular re-encapsulation processes at elevated temperatures, as demonstrated in previous work for gold and alloy nanoparticles (Schadt et al., *Chem. Mater.* 18:5147 (2006); Maye et al., *Langmuir* 16:490 (2000); Zhong et al., *Chem. Commun.* 13:1211 (1999), which are hereby incorporated by reference in their entirety), the examination of the structure and morphology of the evolved nanoparticles is important for the overall assessment of the viability in processing the Fe-oxide@Au nanoparticles. As a control experiment, FIGS. 3A-B show the representative set of TEM images for gold nanoparticles thermally processed from 2-nm sized, DT-capped gold nanoparticles (2.0±0.4 nm). The increased particle size and the high monodispersity of the resulting nanoparticles (6.4±0.4 nm) are consistent with what has been previously reported, demonstrating the effectiveness of the thermal processing condition for processing gold nanoparticles.

Figure 4A:
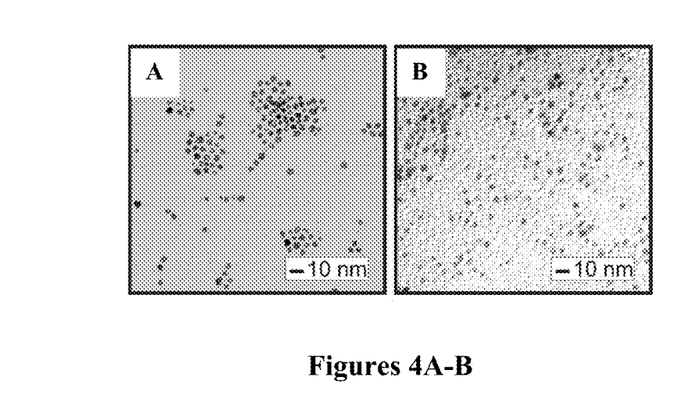

As another control experiment, the thermal processing of $Fe_2O_3$ nanoparticles under the same condition was also examined. FIGS. 4A-B show a representative set of TEM images for $Fe_2O_3$ nanoparticles by thermally processing of $Fe_2O_3$ nanoparticles of 4.4 nm size. The observation of insignificant changes in the particle size and the monodispersity of the resulting nanoparticles (4.5±0.5 nm) demonstrate the absence of any size evolution for $Fe_2O_3$ nanoparticles with the thermal processing conditions used in the present work. The absence of size evolution is likely associated with the lack of significant change in melting temperature for $Fe_2O_3$ nanoparticles. In other words, $Fe_2O_3$ nanoparticles are stable under the thermal processing temperature.

Figure 5A:
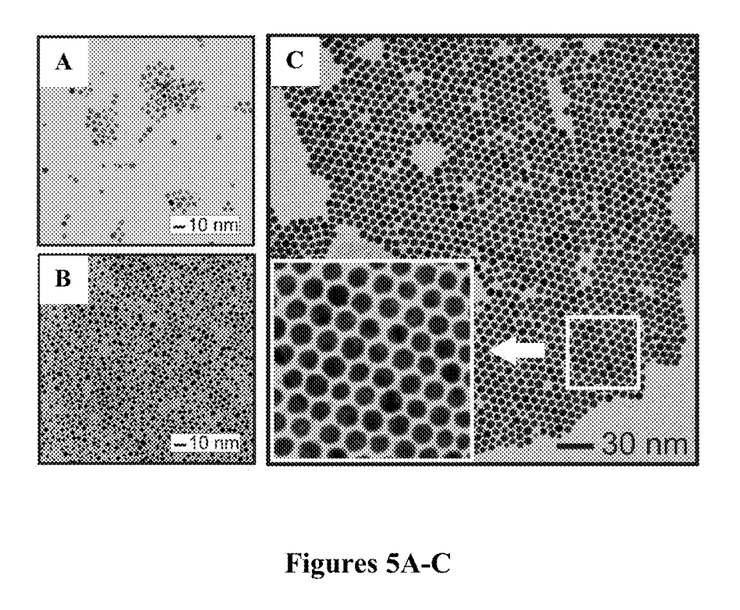

The above two control experiments demonstrate that the gold nanoparticles undergo thermally activated coalescence responsible for the growth of Au nanoparticles whereas the $Fe_2O_3$ nanoparticles remain largely unchanged in this process. In the next experiment, the thermal processing treatment of a controlled mixture of the 2-nm sized gold nanoparticles and the 4-nm sized $Fe_2O_3$ nanoparticles was examined under the same thermal processing condition. Specifically, a toluene solution of the two precursor nanoparticles (e.g., stock solutions of decanethiolate (DT)-capped Au (2 nm, 158 µM) and OAM and/or OA-capped $Fe_2O_3$ (5 nm, 6.3 µM), or $Fe_3O_4$ with a controlled ratio in a reaction tube was heated in an oven at 149° C. for 1 hour. Other constituents in the solution included TOA-Br and DT with controlled concentrations. After cooling to room temperature, the solidified liquid was dispersable in toluene. FIGS. 5A-C show a representative set of TEM micrographs comparing the resulting nanoparticles obtained from the thermal processing treatment with the two precursor nanoparticles. It is evident that highly monodispersed nanoparticles with an average size of 6.2±0.3 nm are obtained from the processing of the mixture using a 25:1 ratio of Au to $Fe_2O_3$ nanoparticles (FIG. 5C). The precursor Fe-oxide nanoparticles were not observed after the processing treatment of the mixture. This feature is in sharp contrast to the morphological features corresponding to the nanoparticle precursors of DT-capped Au (2.1±0.3 nm) (FIG. 5B) and OA-capped $Fe_2O_3$ (4.4±0.3 nm) (FIG. 5A).

Figure 6A:
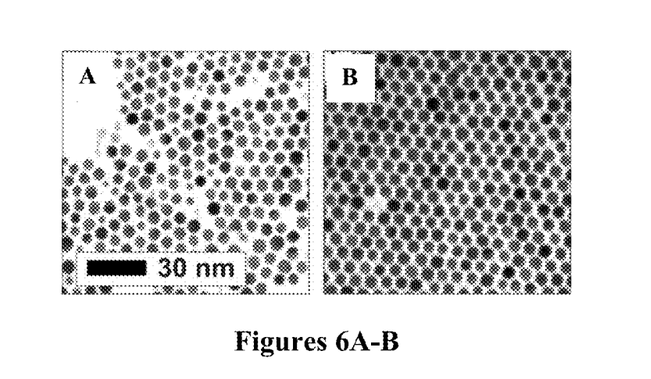

FIGS. 6A-B show another representative set of TEM images for the nanoparticles thermally evolved from the same precursors but with two different molar ratios of the precursors, Au:$Fe_2O_3$=25:1 (FIG. 6A) and 132:1 (FIG. 6B). It is evident that the size and monodispersity of the evolved nanoparticles are dependent on the precursor ratios. A higher ratio of Au to $Fe_2O_3$ nanoparticle precursors clearly favors the formation of larger-sized and more monodispersed nanoparticles.

In addition to manipulating the relative concentrations of Au and $Fe_2O_3$ to control the thickness of Au shell, the formation of the core-shell nanoparticles with multiple magnetic cores were shown to be possible, depending on the manipulation of a combination of control parameters. Nanoparticles with larger sizes (30-100 nm) have been obtained by controlling the ratio of the precursor nanoparticles and the chemical nature of capping molecules. FIGS. 7A-D show a representative set of TEM images for particles obtained with relatively-lower concentrations of Au (Au:$Fe_2O_3$=5:1), demonstrating that important roles have been played by both the Au to $Fe_2O_3$ concentration ratio and the type of capping agent on the final size and monodispersity.

Figure 7A:
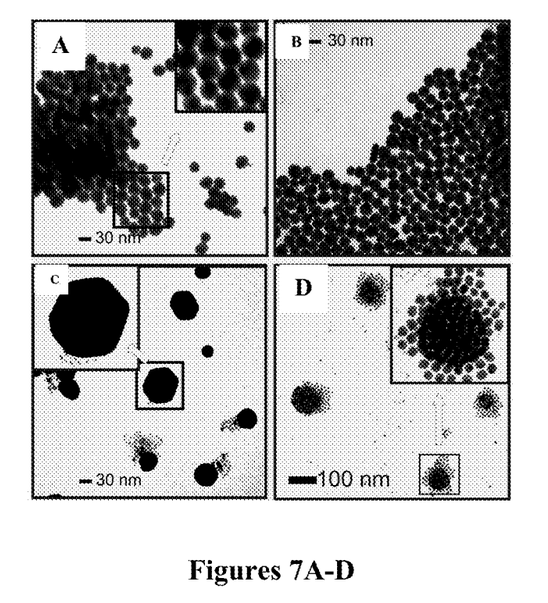

It is also noted that the basic feature of these evolved nanoparticles remains unchanged from sample to sample, demonstrating the reproducibility of the method. The average size for the nanoparticles obtained from OA-capped $Fe_2O_3$ is 31.4±3.0 nm with high monodispersity (FIGS. 7A-B), whereas that from the OAM-capped $Fe_2O_3$ exhibits sizes of 30 to 100 nm and hexagon-shaped features (FIG. 7C).

By controlling the condition so that the thermal equilibrium can be perturbed (e.g., shorter time, lower temperature, or larger reaction volume), the observed features appear to correspond to the early stage of coalescence of the core-shell nanoparticles. For example, for the thermal evolution in a larger reaction volume, spherical clusters with highly ordered packing morphology were observed (FIG. 7D). The center of the spherical assembly shows indications of interparticle coalescence, in contrast to the loosely-bound nanoparticles spread around the spherical outline. Control experiments showed that under the temperature while Au nanoparticles could be evolved to sizes of up to 10 nm, $Fe_2O_3$ nanoparticles remained unchanged. Thus, these large-sized particles likely consist of multiple Fe-oxide cores.

Example 10—Characterization of the Surface Chemistry of the Core-Shell Magnetic Nanoparticles There are two key questions that must be answered about the formation of the core-shell magnetic nanoparticles. The first question concerns whether surface of the nanoparticles are composed of Au shell, and the second question concerns whether the nanoparticle cores include magnetic $Fe_2O_3$ nanoparticles. To address these questions, both high-resolution TEM ("HRTEM") and electron diffraction ("ED") techniques seemed to be ideal for examining the detailed core-shell morphology. While small differences in HRTEM and ED have been observed by comparing the $Fe_2O_3$@Au nanoparticles with the Au and $Fe_2O_3$ nanoparticles, the results were not conclusive. XPS technique is also not appropriate because of the depth sensitivity issue. It is also noted that XRD examination of the core-shell nanoparticles was not conclusive either. It is possible that the lattice parameters of the iron oxide core were distorted by the relatively thick Au shell, which is a fundamental issue to be addressed. Detailed experimental data obtained from the examinations of the core-shell nanoparticles is provided in terms of the surface chemistry of the Au shell and the magnetic properties of the core to address the above two questions.

Figure 8:
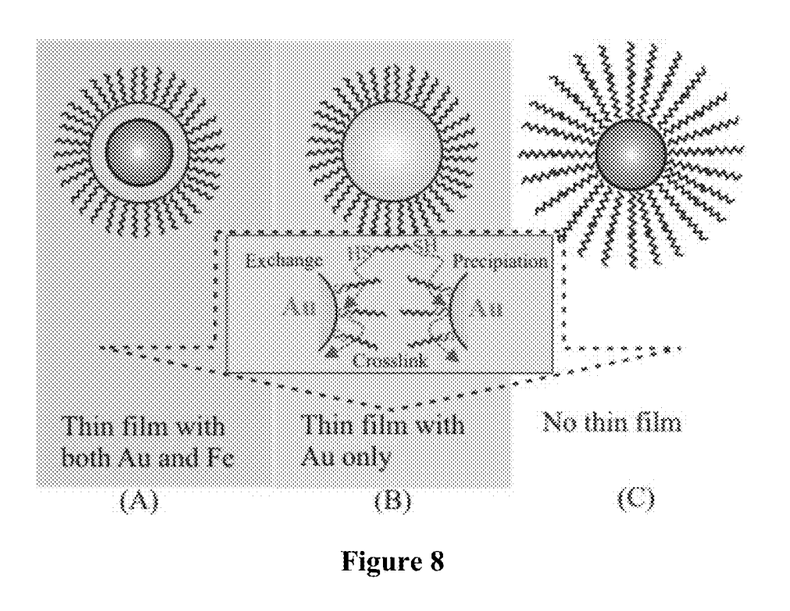
FIG. 8 is a schematic illustration of the dithiolate-gold based binding chemistry for the thin film assembly of $Fe_2O_3$@Au (A), Au (B) and $Fe_2O_3$ (C) nanoparticles on a substrate.

To prove that the resulting nanoparticles include the desired Au shell, two types of measurements were carried out, both of which were based on the surface chemistry of gold-thiolate binding and core-shell composition. First, the core-shell composition was analyzed, for which samples were prepared by assembling the nanoparticles into thin films on a glass substrate using dithiols as linkers/mediators (FIG. 8) (Wang et al., *J. Phys. Chem. B* 109:21593 (2005); Leibowitz et al., *Anal. Chem.* 71:5076 (1999); Luo et al., *J. Phys. Chem.* 108:9669 (2004), which are hereby incorporated by reference in their entirety). The dithiolate-gold binding chemistry involves a sequence of exchanging, cross-linking, and precipitation processes which has previously been demonstrated to occur to Au surface only. Thin film assemblies were observed for those with an Au surface, i.e., $Fe_2O_3$@Au (FIG. 8, (A)) and Au (FIG. 8, (B)) nanoparticles (or a combination of (A) and (B)). In contrast, there were no thin film assemblies for $Fe_2O_3$ nanoparticles under the same reaction condition (FIG. 8, (C)).

To analyze the core-shell composition, samples of the dithiol-mediated thin film assemblies of the nanoparticles were dissolved in aqua regia, and the composition was then analyzed using direct current plasma-atomic emission spectroscopy (DCP-AES) technique. The as-processed nanoparticles were also analyzed for comparison. For example, 1,9-nonanedithiol-mediated assembly of nanoparticles into a thin film (Brust et al., *J. Chem. Soc. Chem. Commun.* 1994:801-802, which is hereby incorporated by reference in its entirety) is selective to Au or $Fe_2O_3$@Au but not to $Fe_2O_3$. As shown in Table 1, both Au and Fe were detected, demonstrating that the nanoparticles contain both Fe and Au components. It is therefore evident that the surface of $Fe_2O_3$ particles must be covered by Au.

TABLE 1

Analysis of Metal Composition in the $Fe_2O_3$@Au Nanoparticles

| Sample | Atomic ratio (Au:Fe) | $d_{shell}$ (nm) determined by TEM | $d_{shell}$ (nm) determined by DCP-AES |
|---|---|---|---|
| As-synthesized | 77:23 | 1.1 | 1.0 |
| Thin Film | 84:16 | 1.1 | 1.4 |

Quantitatively, the Au:Fe ratios for the thin films were slightly higher than those for the as-synthesized particles. The Au shell thickness can be estimated from the Au:Fe ratios based on a spherical core-shell model (Wang et al., *J. Phys. Chem. B* 109:21593 (2005), which is hereby incorporated by reference in its entirety). The results obtained from the DCP data for both the as-synthesized and the thin film (Table 1) are found to be very close to the values measured from the TEM data.

Figure 9A:
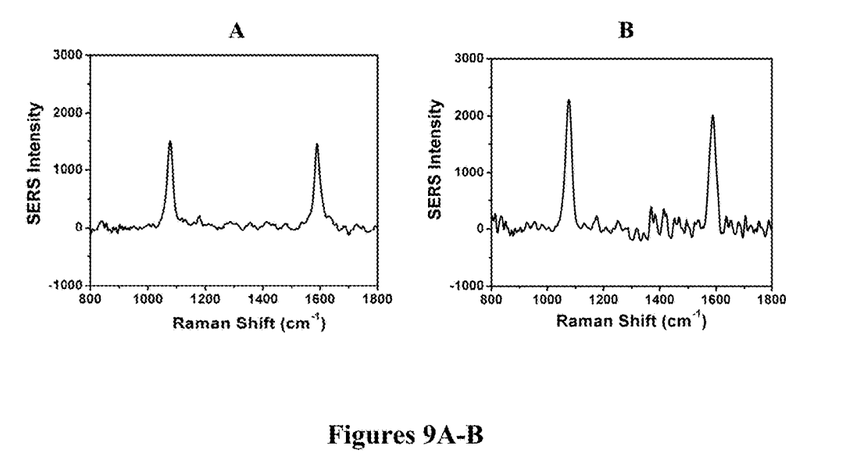

In the second type of measurements, SERS labels such as MBA were immobilized on the surface of the core-shell nanoparticles via Au-thiolate binding chemistry. FIGS. 9A-B show a representative set of SERS spectra for the core-shell $Fe_2O_3$@Au nanoparticles labeled with MBA. The SERS for $Fe_2O_3$@Au nanoparticles (FIG. 9A) showed clearly two peaks at 1084 and 1593 $cm^{-1}$, which are identical to those observed for the Au nanoparticles (FIG. 9B). These two bands correspond to v(CC) ring-breathing modes of MBA, which are characteristic of the expected signature (Varsanyi, *Assignments for Vibrational Spectra of Seven Hundred Benzene Derivatives*; John Wiley & Sons: New York, 1974, which is hereby incorporated by reference in its entirety). Controlled experiment with $Fe_2O_3$ nanoparticles incubated with MBA did not show any of these bands. This observation demonstrates that MBA labels are immobilized on the Au shell of the $Fe_2O_3$@Au nanoparticles.

Figure 10A:
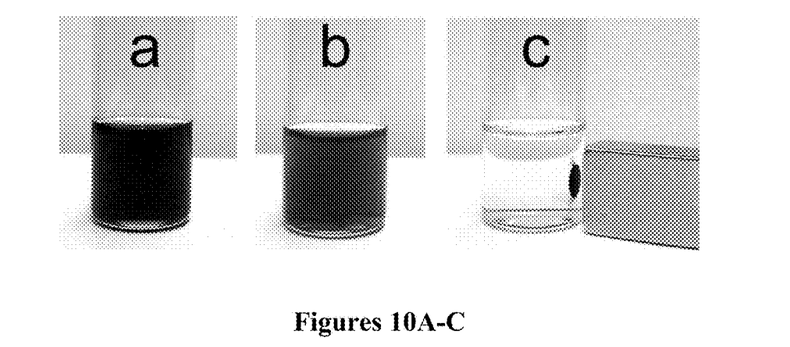

Example 11—Protein Binding and Bioseparation Using the Core-Shell Magnetic Nanoparticles For the targeted bio-separation application, both the protein-binding properties of the gold shell and the magnetic properties of the core in the $Fe_2O_3$@Au nanoparticles are essential. The recent results of magnetic characterization for similar core-shell Fe-oxide@Au nanoparticles (Wang et al., *J. Phys. Chem. B* 109:21593 (2005), which is hereby incorporated by reference in its entirety) have revealed detailed information for assessing the magnetic properties. In FIGS. 10A-C, a set of photos is shown to illustrate the movement of the nanoparticles dispersed in solutions before and after applying a magnetic field (NdFeB type) to the particles. The core-shell nanoparticles can be fully dispersed in toluene solution (FIG. 10A), which did not respond to external magnetic field of the magnet. However, the suspension of the same nanoparticles in ethanol-toluene (FIG. 10B), which has an increased magnetic susceptibility due to aggregation, showed that the suspended particles moved towards the wall near the magnet gradually (FIG. 10C), eventually leaving a clear solution behind.

This test result demonstrated clearly that the $Fe_2O_3$@Au nanoparticles are magnetically active, which is desired for the targeted bio-separation application. Similar results were also obtained for the core-shell nanoparticles prepared using different precursor ratios.

Figure 11A:
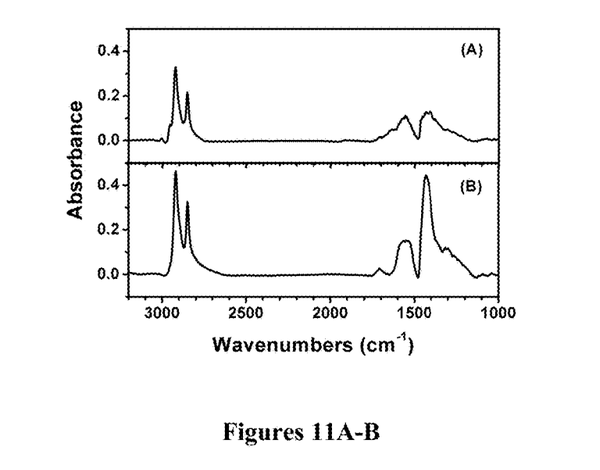

To further demonstrate the viability of the $Fe_2O_3$@Au nanoparticles for magnetic bio-separation, the following proof-of-concept demonstration experiment exploits both the magnetic core and the bio-affinity of the gold shell. In this experiment, the gold-based surface protein-binding reactivity and the Fe-oxide based magnetic separation capability were examined. The DT-capped $Fe_2O_3$@Au particles were first converted to water-soluble particles by ligand exchange reaction with MUA. The ligand exchange reaction involved replacement of the original capping molecules (OAM and OA) on $Fe_2O_3$@Au nanoparticles by acid functionalized thiols. To prove the ligand exchange on the nanoparticle surface, FIGS. 11A-B show a representative set of FTIR spectra of the OAM/OA-capped $Fe_2O_3$@Au nanoparticles before and after the ligand exchange reaction. After the exchange reaction, the band at 3004 $cm^{-1}$ corresponding to the C—H stretching mode next to the double bond from OA and OM capping molecules (FIG. 11A) are clearly eliminated (FIG. 11B). In the meantime, the band at 1709 $cm^{-1}$ corresponding to the carboxylic acid group of MUA is detectable after the exchange reaction. Furthermore, the spectral change in the 1300-1560 $cm^{-1}$ region seemed to support the presence of bands corresponding to the symmetric and asymmetric stretching modes in the carboxylate groups of MUA.

These observations demonstrate the successful exchange of the MUA with the original ligands on the nanoparticles. This is further evidenced by the fact that the post-exchanged core-shell nanoparticles became water-soluble.

The MUA-capped $Fe_2O_3$@Au nanoparticles in water underwent further exchange reaction with a protein-coupling agent, DSP, forming a DSP-derived monolayer on the gold surface. Antibody (anti-rabbit IgG) was then immobilized onto the resulting nanoparticles via coupling with the surface DSP, forming Ab-immobilized core-shell nanoparticles.

Figure 12:
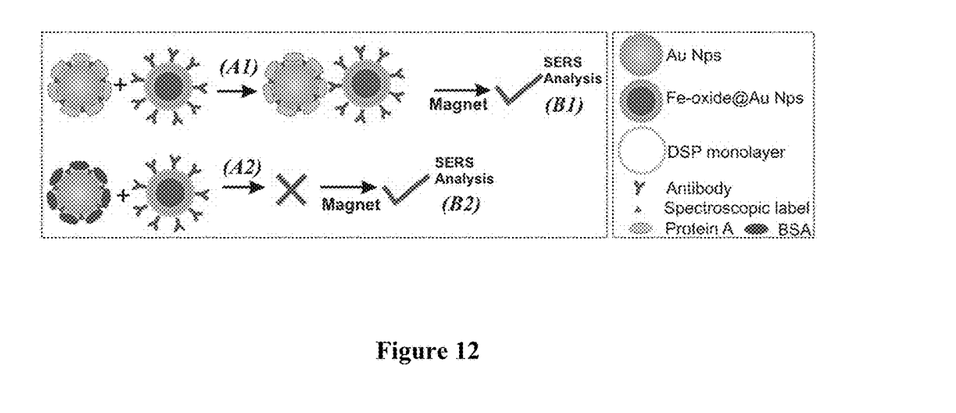
FIG. 12 is an illustration of the reactions and product separation of antibody-labeled $Fe_2O_3$@Au nanoparticles in two different reaction systems: (A1-B1): reaction with protein A capped gold nanoparticles, and (A2-B2): reaction with BSA capped gold nanoparticles. In both cases, the SERS Label (L) mercaptobenzoic acid (MBA); Antibody (Ab): anti-rabbit IgG.

The Ab-immobilized core-shell nanoparticles were reacted with Au particles capped with both protein-A and a Raman label, e.g., MBA. FIG. 12 illustrates the reactions and product separation of the antibody-labeled $Fe_2O_3$@Au nanoparticles in two different reaction systems: reaction with protein A capped gold nanoparticles (A1-B1), and reaction with BSA capped gold nanoparticles (A2-B2). In each case, magnetic field was applied to collect the magnetically-active products for SERS analysis.

Figure 13:
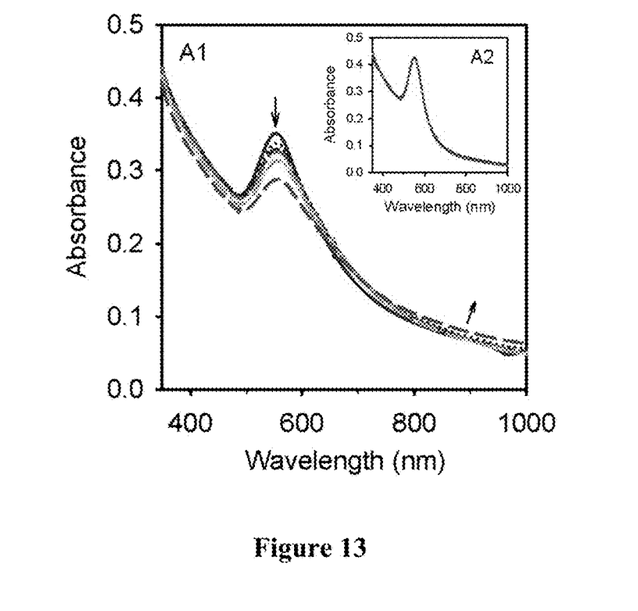
FIG. 13 is a UV-Vis spectra monitoring the reaction between Au/Protein-A/L and $Fe_2O_3$@Au/Ab (A1). Inset: the spectra monitoring the reaction between Au/BSA/L and $Fe_2O_3$@Au/Ab (A2). The spectra were recorded as a function of time (within 1 hr). The arrows indicate the direction of the spectral evolution as a function of time.

FIG. 13 shows a representative set of UV-Vis spectra monitoring the reaction progress. Results from control experiments are also included for comparison, in which the Au particles capped with BSA (bovine serum albumin) and MBA were used to replace the Au particles capped with protein A while maintaining the rest of the conditions. The specific reactivity between $Fe_2O_3$@Au nanoparticles capped with anti-rabbit IgG (Ab) and Au nanoparticles capped with protein-A is clearly evidenced by the gradual decrease of the surface plasmon (SP) resonance band at 535 nm and its expansion at the longer wavelength region (A1). This finding is in sharp contrast to the lack of any change in SP band for the reaction between $Fe_2O_3$@Au nanoparticles capped with anti-rabbit IgG and Au nanoparticles capped with BSA (A2). In contrast to the specific binding of anti-rabbit IgG to protein-A, there is no specific binding between BSA and anti-rabbit IgG.

Figure 14:
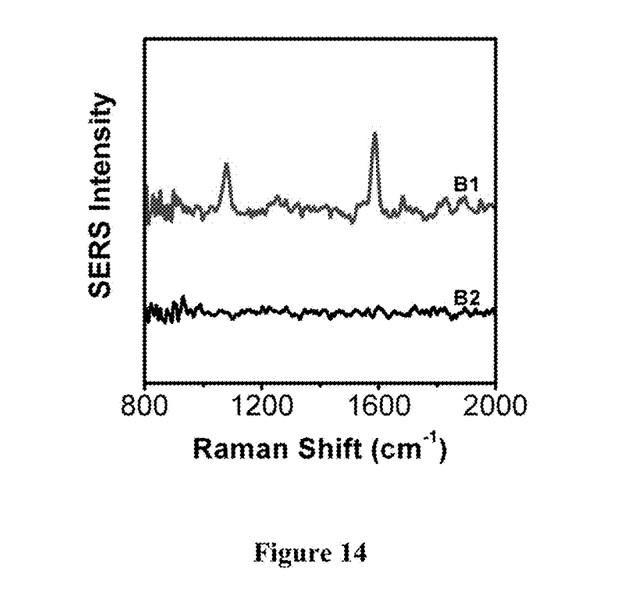
FIG. 14 is a SERS spectra of the products from the reactions between Au/Protein-A/L and $Fe_2O_3$@Au/Ab and between Au/BSA/L and $Fe_2O_3$@Au/Ab (A2). A magnet was used to collect the particles, which were then deposited on a Au substrate. SERS Label (L): MBA. Antibody (Ab): anti-rabbit-IgG.

FIG. 14 shows a representative set of SERS spectra of the products collected by applying the magnet to the reaction solution for the $Fe_2O_3$@Au nanoparticles capped with anti-rabbit IgG and Au nanoparticles capped with protein-A. The spectrum from the control experiment is also included for comparison, in which the Au nanoparticles capped with BSA protein and MBA label were used to react with $Fe_2O_3$@Au nanoparticles capped with anti-rabbit IgG while maintaining the reaction conditions.

The product of the reaction collected by a magnet showed the expected SERS signature of MBA (B1), corresponding to $\nu$(C—C) ring-breathing modes of MBA. This finding is in sharp contrast to the absence of SERS signature in the control experiment (B2). These two findings clearly demonstrate the viability of exploiting the magnetic core and gold shell of the $Fe_2O_3$@Au nanoparticles for interfacial bio-assay and magnetic bio-separation.

In conclusion, a novel strategy based on the thermally-activated hetero-coalescence between Au and $Fe_2O_3$ nanoparticles has been demonstrated for the fabrication of monodispersed magnetic core-shell nanoparticles, $Fe_2O_3$@Au. Similar results have also been observed for $Fe_3O_4$ nanoparticle cores. In comparison with the previous sequential synthesis method involving reduction and deposition of gold onto pre-synthesized iron oxide nanoparticles (Wang et al., *J. Phys. Chem. B* 109:21593 (2005), which is hereby incorporated by reference in its entirety), the nanoparticles made by the thermal approach can have similar core-shell structure with gold shell and iron-oxide core, and show similar behavior in forming thin films due to the gold shell. Some of the major differences between the two nanoparticle products include the core-shell size range and the surface capping structure. Due to the unique processing environment, nanoparticles with much larger sizes can be made. The capping structure can be tailored differently in the two cases. These core@shell nanoparticles consist of magnetically-active Fe-oxide core and thiolate-active Au shell, which were shown to exhibit the Au surface binding properties for interfacial biological reactivity and the Fe-oxide core magnetism for magnetic bio-separation. These magnetic core-shell nanoparticles have therefore shown the viability for utilizing both the magnetic core and gold shell properties for interfacial bio-assay and magnetic bio-separation. These findings are entirely new, and could form the basis of fabricating size, magnetism, and surface tunable magnetic nanoparticles for bio-separation and biosensing applications.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. Core-shell nanoparticles, each core-shell nanoparticle comprising:
   a shell containing a gold-silver mixture;
   a plurality of discrete, nonconcentric, cores containing an iron-cobalt mixture, each core being within and surrounded by said shell; and
   a ligand cap over said shell.

2. The core-shell nanoparticles according to claim 1, wherein the nanoparticles are present in a monodispersion with controlled diameters ranging from 5 nm to 100 nm.

3. The core-shell nanoparticles according to claim 1, wherein the iron in the core is an iron oxide which is magnetic, paramagnetic, or superparamagnetic.

4. The core-shell nanoparticles according to claim 1, wherein the iron in the core is an iron oxide-containing core comprising a compound selected from the group consisting of $Fe_3O_4$ and $Fe_2O_3$.

5. The core-shell nanoparticles according to claim 4, wherein the iron in the core is an iron oxide-containing core comprising $Fe_2O_3$.

6. The core-shell nanoparticles according to claim 1, wherein the ligand cap is selected from the group consisting of decanethiolate, oleylamine, oleic acid, acrylates, N,N-trimethyl(undecylmercapto)ammonium (TUA), tetrabutylammonium tetrafluoroborate (TBA), tetramethylammonium bromide (TMA), cetyltrimethylammonium bromide (CTAB), citrates, poly methacrylate, ascorbic acid, DNA, 2-mercaptopropionic acid (MPA), 3-mercaptopropionic acid (MPA), 11-mercaptoundecanoic acid (MUA), 10-mercaptodecane-1-sulfonic acid, 16-mercaptohexadecanoic acid, diimide, N-(2-mercaptopropionyl)glycine (tiopronin), 2-mercaptoethanol, 4-mercapto-1-butanol, dodecyl sulfate, amino acids, homocysteine, homocystine, cysteine, cystine, glutathione, mercaptobenzoic acid (MBA), Protein A, bovine serum albumin (BSA), and anti-rabbit-IgG (Ab).

7. The core-shell nanoparticles according to claim 6, wherein the ligand cap is selected from the group consisting of decanethiolate, oleylamine, and oleic acid.

8. The core-shell nanoparticles according to claim 7, wherein the ligand cap is decanethiolate.

9. The core-shell nanoparticles according to claim 7, wherein the ligand cap is oleylamine.

10. The core-shell nanoparticles according to claim 7, wherein the ligand cap is oleic acid.

11. The core-shell nanoparticles according to claim 1 further comprising:
    a first binding material bound to the ligand-capped shell.

12. The core-shell nanoparticles according to claim 11, wherein the first binding material is selected from the group consisting of proteins, peptides, antibodies, and antigens.

* * * * *